(12) United States Patent
Johnstone et al.

(10) Patent No.: US 6,702,995 B1
(45) Date of Patent: Mar. 9, 2004

(54) DELIVERY SYSTEM

(75) Inventors: Robert Alexander Walker Johnstone, Bebington (GB); Hilmar Meek Warenius, Heswall (GB); Thelmo Luis Coutinho Figueiredo, Pataias (PT); Alexandra Maria Sørensen, Gentofte (DK)

(73) Assignee: TheRyte, Ltd., Liverpool (GB)

( * ) Notice: Subject to any disclaimer, the term of this patent is extended or adjusted under 35 U.S.C. 154(b) by 0 days.

(21) Appl. No.: 09/529,133

(22) PCT Filed: Oct. 9, 1998

(86) PCT No.: PCT/GB98/03046

§ 371 (c)(1), (2), (4) Date: Jun. 29, 2000

(87) PCT Pub. No.: WO99/18998

PCT Pub. Date: Apr. 22, 1999

(30) Foreign Application Priority Data

Oct. 9, 1997 (GB) .............................................. 9721367

(51) Int. Cl.$^7$ ........................ A61K 51/00; A61M 36/14
(52) U.S. Cl. ........................ 424/1.65; 424/1.11; 424/9.1
(58) Field of Search .............................. 424/1.11, 1.65, 424/9.1, 9.2

(56) References Cited

U.S. PATENT DOCUMENTS 5,576,012 A    11/1996   Bauer et al.

FOREIGN PATENT DOCUMENTS

| | | |
|---|---|---|
| EP | 0583955 | 2/1994 |
| EP | 0822217 | 2/1998 |
| WO | 9210211 | 6/1992 |
| WO | 9710849 | 3/1997 |
| WO | 9741894 | 11/1997 |

OTHER PUBLICATIONS

International Search Report for PCT/GB98/03046.

*Primary Examiner*—Dameron L. Jones
(74) *Attorney, Agent, or Firm*—Rothwell, Figg Ernst & Manbeck

(57) ABSTRACT

The present invention relates to a delivery system useful for water-insoluble drugs, therapeutic agents, and diagnostic agents. More particularly, it relates to a method of packaging water-insoluble substances such as, for example, a drug or other therapeutic or diagnostic agent, to facilitate uptake into the human or animal body and to substances packaged by this method. The packaging method renders the water-insoluble substance water-soluble by packaging it in an amphiphilic polymer that is soluble in water. The invention also relates to a method of treating cancer through administering a water-insoluble drug or other therapeutic or diagnostic agent packaged according to the method describe above.

16 Claims, 3 Drawing Sheets

DELIVERY SYSTEM

This is a 371 of application Ser. No. PCT/GB98/03046, filed Oct. 9, 1998.

The present invention relates to a delivery system. More particularly it relates to a method of packaging a water-insoluble substance, such as, for example, a drug or other therapeutic or diagnostic agent, to facilitate uptake into the human or animal body and to the so packaged substance. It also relates to the use of an amphiphilic polymer in the manufacture of a medicament.

Many substances, both natural and manmade, whilst having potential as drugs or other therapeutic or diagnostic agents are rejected in early studies because they are water-insoluble both in in-vitro cell culture and subsequent in-vivo phase I clinical studies.

Current attempts to deliver water-insoluble substances in medicaments mostly involve some form of encapsulation (not an ideal solution because of the complex chemistry involved in getting uniform release of the active substance), micelle or similar formation using lipid-like materials (not ideal because each active substance needs it own special formulation and the micelles are dynamic systems that open and close regularly so that the agent is lost prematurely) or use of a water-miscible solvent such as dimethyl sulphoxide (not a desired solution because of the need to inject or apply solvent into human metabolic systems).

It is an aim of the present invention to produce a water-solubilized form of a water-insoluble substance.

According to one aspect of the present invention there is provided a water-solubilized form of a water insoluble drug or other therapeutic or diagnostic agent characterised in that the water insoluble drug or other therapeutic or diagnostic agent is packaged in an amphiphilic polymer which is miscible with water.

The drug or other therapeutic or diagnostic agent is carried internally within a hydrophobic or lipophilic pocket or pockets defined by the conformation of said polymer in the aqueous environment.

Thus, in an aqueous system, the water-insoluble substance is carried in the hydrophobic or lipophilic pocket or pockets of the amphiphilic polymer, the latter (and therefore the whole system) being soluble in water. On reaching for example a cell membrane, the amphiphilic polymer cannot cross the membrane because of its size but it can undergo a conformational change to release its contents, namely the water-insoluble substance, to the cell wall.

The amphiphilic polymer is preferably a copolymer comprising hydrophilic monomers and hydrophobic monomers.

An advantage of the amphiphilic polymer is its ability per macromolecule to carry several molecules of the drug or other therapeutic or diagnostic agent (often about 5 to 20) internally within the hydrophobic or lipophilic pocket. This means less amphiphilic polymer is required per unit of drug or other therapeutic or diagnostic agent than other carriers.

A further advantage of the amphiphilic polymer is that it allows attachment of cell or tissue specific molecules such as, for example, antibodies. The attachment of such molecules provides a means of targeting drugs contained within the amphiphilic polymer. In addition, a major problem with therapeutic antibody targeting at present is that the relatively small number of antigenic sites on cells restricts the maximum concentration of drug or other therapeutic agent that can be delivered to the cell. By labeling the amphiphilic polymer it should be possible to deliver much higher concentrations of the drug or other therapeutic or diagnostic agent to the cell. By attaching the amphiphilic polymer to, for example, an antibody, it would be possible to target tumour or other cells with high concentrations of the water-insoluble drug by presenting them to the tumour or other cells using the amphiphilic polymer as a carrier.

Another characteristic of the amphiphilic polymers lie in their electronic charge, which means in solution they can flow under the influence of an electrical potential gradient. Thus, with the drug or other therapeutic or diagnostic agent carried within a pocket or pockets defined by the confirmation of said polymer in the aqueous environment the packaged drug or other therapeutic or diagnostic agent can be moved through a tissue under the influence of an electrical potential gradient. This ability would be advantageous in techniques in which molecules are transported from the surface of the skin to deeper layers by an electrical gradient.

Preferred amphiphilic polymers include: polymers comprising at least one hydrophilic group and at least one hydrophobic group, such that the ratio of hydrophilic groups to hydrophobic groups lies in the range from 1:10 to 10:1; preferably from 1:3 to 3:1.

More preferably the amphiphilic polymers will comprise regions which are hydrophobic and regions which are hydrophilic in nature. As a consequence of the polymer having regions of differing hydrophobicity/hydrophilicity the polymer takes up a confirmation in an aqueous environment in which the hydrophobic regions are generally presented internally and the hydrophilic regions are generally presented externally. This results in the formation of a hydrophobic or lipophilic pocket or pockets which can be used to carry water-insoluble drugs or other therapeutic or diagnostic agents.

The hydrophobic groups or regions interact with the water insoluble drug or other therapeutic or diagnostic agent through hydrophobic non-bonded interactions such as dispersion forces, Π—Π interactions, and/or charge transfer interactions, and/or Van der Waals interactions which stabilise the composition in a pocket or pockets while the hydrophilic groups of the polymer solubilise the composition. When acting by charge transfer interactions, an electron donor-acceptor complex is formed.

Preferred polymeric structures for solubilisation of a drug or other therapeutic or diagnostic agent include the following:

Structure of Formula I.

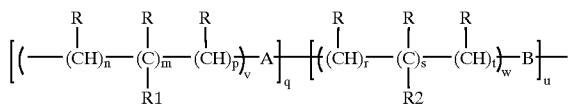

where A and B are selected from: $CH_2$, NH, O, ketone, an ester linkage, an amide linkage (—CO—NR—), and an imine linkage (—CR=N—);

where n,m,p,r,s,t can independently be any whole number as long as $(n+m+p)_v + (r+s+t)_w$ ranges from 1–1000, preferably from 1–500 and such that the ratio v/w varies between 0.1 and 1;

where the values of q and u, independently lie in the range from 1–10;

Each R, independently, can be selected from H, alkyl, haloalkyl, alkenyl, and alkynyl; preferably H or $CH_3$;

R1 is selected from (partially) hydrophobic moieties containing aromatic hydrocarbon rings derived from compounds such as toluene, methyl styrene, stilbene, pyridine, naphthalene, anthracene, phenanthrene, phenyl, histidine, tryptophan, phenyl alanine, tyrosine, alkyl benzene, xylenes, carbazoles, xanthenes, acridines, purines, pyridazines and indoles;

R2 is selected to provide water-solubility and these substituents are therefore hydrophilic in nature such as —OH, hydroxylalkyl such as hydroxymethyl and hydroxyethyl; polyoxyethylene, hydroxyphenyl and derivatives thereof, moieties derived from pyrrolidine, pyridinre-N-oxide, N-oxide derivatives of histidine, tryptophan, phenyl alanine, tyrosine; phenyl sulphonate, naphthalene sulphonate, imidazole, water-soluble salt derivative of naphthalene, anthracene, phenanthrene, phenyl, carbazoles, xanthenes, acridines, purines, pyridazines, indoles, —COOH, —COOM, —SO₃M where M is an alkali metal ion; —NR₂, —NR₃⁺X⁻ where X is a halide ion and R is independently selected from H, alkyl, and hydroxyalkyl;

R1 and R2, independently, can be substituents on the moieties A and B in the event that A and/or B are not an ether, ketone, amide, imine, or ester linkage.

Substituted polysaccharides of the unit structure

where C and D are oligosaccharide units and where oligosaccharide units comprise the product of polycondensation of monosaccharides by O-glycosidic linkage containing up to 10 such residues selected from hexose, pentose and deoxyhexose residues;

where the values of q and u, independently, lie in the range from 1 to 10;

where the substituent R1 is selected from (partially) hydrophobic moieties containing aromatic hydrocarbon rings derived from compounds such as toluene, methyl styrene, stilbene, pyridine, naphthalene, anthracene, phenanthrene, phenyl, histidine, tryptophan, phenyl alanine, tyrosine, alkyl benzene, xylenes, carbazoles, xanthenes, acridines, purines, pyridazines and indoles; and R2 is selected to provide water-solubility and these substituents are therefore hydrophilic in nature such as —OH, hydroxylalkyl such as hydroxymethyl and hydroxyethyl; polyoxyethylene, hydroxyphenyl and derivatives thereof, moieties derived from pyrrolidine, pyridine-N-oxide, N-oxide derivatives of histidine, tryptophan, phenyl alanine, tyrosine, phenyl sulphonate, naphthalene sulphonate, imidazole, water-soluble salt derivative of naphthalene, anthracene, phenanthrene, phenyl, carbazoles, xanthenes, acridines, purines, pyridazines, indoles, —COOH, —COOM, —SO₃M where M is an alkali metal ion; —NR₂, —NR₃⁺X⁻ where X is a halide ion and R is independently selected from H, alkyl, and hydroxyalkyl.

Polymers having a unit structure of the formula III.

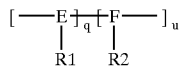

where E and F are di-substituted aromatic moieties such as phenylene, naphthalene, phenanthroline, anthracene, thiophene;

where the value of q and u, independently, lie in the range from 1 to 10;

R1 is selected from (partially) hydrophobic moieties containing aromatic hydrocarbon rings derived from compounds such as toluene, methyl styrene, stilbene, pyridine, naphthalene, anthracene, phenanthrene, phenyl, histidine, tryptophan, phenyl alanine, tyrosine, alkyl benzene, xylenes, carbazoles, xanthenes, acridines, purines, pyridazines and indoles; and R2 is selected to provide water-solubility and these substituents are therefore hydrophilic in nature such as —OH, hydroxylalkyl such as hydroxymethyl and hydroxyethyl; polyoxyethylene, hydroxyphenyl and derivatives thereof, moieties derived from pyrrolidine, pyridine-N-oxide, N-oxide derivatives of histidine, tryptophan, phenyl alanine, tyrosine, phenyl sulphate, naphthalene sulphonate, imidazole, water-soluble salt derivative of naphthalene, anthracene, phenanthrene, phenyl, carbazoles xanthenes, acridines, purines, pyridazines, indoles, —COOH, —COOM, —SO₃M where M is an alkali metal ion; —NR₂, —NR₃⁺X⁻ where X is a halide ion and R is independently selected from H, alkyl, and hydroxyalkyl.

The molecular weight of the amphiphilic oligomer or polymer is preferably in the range of from 500 to 1,000,000 D more preferably from 1000 to 500,000 D and most preferably 30,000 to 150,000 D.

The amphiphilic polymers described above can be random, graft, or block polymers.

The amphiphilic polymers can also contain more than two different monomers as long as the ratio of hydrophilic and hydrophobic groups lies in the range from 1:10 to 10:1; preferably from 1:3:3:1.

Preferred amphiphilic polymers are aromatic amphiphilic polymers selected from: polystyrene sodium sulphonate-co-vinyl naphthalene, polyvinyl pyrrolidone-co-vinyl imidazole, and polynaphthalene sulphonate (TAMOL®).

A more preferred copolymer is polystyrene sodium sulphonate-co-vinyl naphthalene.

Furthermore, the polymer can be a homopolymer which exhibits amphiphilic character such as partially neutralised polymethacrylic acid.

There is also another special group of saccharides that are suitable for the solubilisation of a drug or other therapeutic or diagnostic agent which are the cyclic polysaccharides such as natural cyclodextrins and modified cyclodextrins.

According to a further aspect of the present invention there is provided the use of an amphiphilic polymer in the manufacture of a medicament.

In one embodiment the therapeutic substances are those used in inhalants. The amphiphilic polymers of the invention could thus provide novel vehicles for solubilizing and delivering therapeutic substances to the mucosal lining of the lungs in inhalants, nebulisers etc. such as those used in the treatment of asthma.

It is another aim of the present invention to provide a way of packaging water-insoluble substances in order that they might be used as medicaments.

According to this aspect of the present invention there is provided a method of solubilising a water-insoluble drug or other therapeutic or diagnostic agent comprising packaging said drug or other therapeutic or diagnostic agent in an amphiphilic polymer which is miscible in water.

The drug or other therapeutic or diagnostic agent may be packaged as a water solubilized medicament or diagnostic tool using, for example, one of the following methods:

Preparation of Water-soluble Medicament

The process for making the water-soluble medicament comprises the following steps:

a-dissolving the drug or other therapeutic or diagnostic agent in a water miscible organic material;

b-dissolving said polymer in $H_2O$;

c-adding said predissolved polymer to the predissolved drug or other therapeutic or diagnostic agent or vice versa d-adding as much water as may be necessary for dilution slowly with stirring; and e-optionally removing the water miscible organic material by evaporation and the water by freeze drying.

The water miscible organic material may be any pharmaceutically acceptable material in which a drug or other therapeutic or diagnostic agent is soluble. A suitable material is a water-miscible organic solvent selected from methanol, ethanol, isopropanol, n-propanol, acetone, n-methylpyrrolidone and dimethylformamide, preferably methanol, ethanol, ethanol, isopropanol, n-propanol or acetone.

A particularly preferred water miscible material for the production of the water-soluble medicament in liquid form is a nonionic surfactant of formula

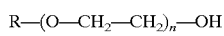

where R is a $C_8$–$C_{22}$ alkyl; and where n lies in the range from 2 to 24, preferably 7.

Alternately a water-soluble medicament may be prepared by a) -Synthesis from solution or from a polymer melt or b) -Isolation as a pure solid a) -Synthesis of the Water-soluble Medicament

1. -From solution, the synthesis comprises the following steps:

i) the drug or other therapeutic or diagnostic agent is dissolved in a water miscible organic solvent, for example dimethylsulfoxide (DMSO) or dimethyl formamide (DMF).

ii) -dissolution or addition of the solid polymer to this solution, and iii) -Addition of sufficient water to yield the required solution strength while the mixture is stirred continuously.

b-Isolation of the Water-soluble Medicament

1. -Isolation of the medicament as a pure solid. An aqueous solution of the amphiphilic polymer containing the therapeutic agent is mixed with an excess of acetone. During 2–4 hours a precipitate is formed which is isolated using suction filtration followed by vacuum drying. The resulting solid can be redissolved in water as needed.

2. -From a polymer melt the synthesis comprises the following steps: the drug or other therapeutic or diagnostic agent is dissolved in molten polymer and stirred for half an hour. After cooling, the resulting solid can be added to water in order to prepare an aqueous solution of the water solubilized therapeutic agent.

3. -A solution of the therapeutic agent plus amphiphilic polymer together in a organic solvent is evaporated to dryness. The resulting solid may be dissolved in water and filtered if necessary to yield a water solubilized form of the therapeutic agent.

The amphiphilic polymers of the invention offer many potential medical applications 1) they could, for example, be used to test potentially therapeutically active drugs, 2) they could also provide an alternative vehicle for the delivery of some of the presently available drugs which require special techniques and reagents to make them soluble. 3) they might also be of value in carrying insoluble therapeutic molecules through the skin or to mucus membranes and 4) they might also allow insoluble agents with cancer specific localisation, ie. fluorinated porphyrins to be used in nmr spectroscopy and imaging of cancer.

The invention will be further described by way of example only with reference to the following example compositions and test data.

Example of Delivery of a Photochemical Sensitizer to a Culture of Cancer Cells (Molt 4)

(i) Preparation of an Aqueous Solution of a Water-insoluble Sensitizer

Typically, between 0.3 and 0.5 g of an amphiphilic polymer eg. polystyrene sodium sulphonate co vinyl naphthalene and 2–4 mg of a sensitizer eg 5,10,15,20 tetrakis phenyl porphyrin were dissolved in approximately 0.5 mL of dimethylformamide by stirring the ingredients together for about 5 minutes at room temperature. The dimethylformamide was evaporated off under reduced pressure. To the residue was added 1 L of distilled water and the whole was stirred for 24 hours in the dark at about 50° C. After this period, the solution was filtered through a 0.22 μm pore size filter (Millipore) to give a clear solution. The exact concentration of sensitizer in the amphiphilic polymer was determined by analysis. Typically, for a porphyrin sensitizer, the concentration was determined by ultraviolet/visible measurement of absorption at the Soret wavelength near 420 nm.

(ii) Preparation of Cell Growth Medium

The cell growth medium was prepared in three varieties. Each variety contained the nutrients required for cell growth. One variety contained neither sensitizer nor polymer, a second contained polymer but no sensitizer and a third contained both polymer and sensitizer.

Into a flask were mixed RPMI (Roswell Park Memorial Institute) tissue culture medium; from Gibco-BRL; 10 mL at 10 times normal concentration, aqueous sodium bicarbonate solution (3 mL of 7.5% w/v), L-glutamine (1 mL; 2 mM), penicillin and streptomycin (1 mL; 50 μmg/mL) and the sensitizer solution prepared as in (i) above (85 mL). The resulting solution was adjusted to pH 7.2 by careful addition of aqueous sodium hydroxide solution (5 M) and finally once more filtered through a 0.22 μm filter. The resulting solution was used as the growth medium containing both sensitizer and polymer in the following experiments. A growth medium containing only polymer was prepared as here but omitting the sensitizer, viz, instead of the sensitizer solution (85 mL), an equal volume of distilled water containing the same amount of polymer but no sensitizer was added. For the growth medium containing no sensitizer and no polymer, only distilled water (85 mL) was used in the above formulation in place of the sensitizer solution.

(iii) Testing the Effect of the "Water-insoluble" Sensitizer Held in Aqueous Solution by the Amphiphilic Polymer For this testing, three series of solutions were prepared. For any one concentration of a particular sensitizer, the three solutions were:

(a) A control, consisting of only the growth medium with no sensitizer and no polymer present.

(b) A solution containing the growth medium plus polymer but with no sensitizer present.

(c) A solution containing the growth medium plus polymer plus sensitizer.

For each growth medium, 10 mL of a suspension containing $10^7$–$10^8$ cells/mL were centrifuged and the cells were resuspended in one of the growth media described above (45mL) to give three cell preparations: A, containing sensitizer plus polymer; B, containing neither sensitizer nor polymer; C, containing polymer but no sensitizer. Serum (5 mL) was added to each flask and the cells were incubated at 37° C. for 24 hours. Thus during cultivation, one set of cells was exposed to sensitizer plus polymer, one set to neither sensitizer nor polymer and a third set to polymer but not sensitizer. The flasks A,B,C were taken from the incubator. A cell count showed no significant difference in the numbers of cells in each growth medium. Thus, cell growth was not inhibited by either the sensitizer or the polymer. The contents of flask A containing both sensitizer and polymer were divided into two approximately equal parts ($A_1$, $A_2$). Part $A_1$ was reserved. Part $A_2$ was centrifuged down and the supernatant liquid medium was removed; the cells were washed three times by resuspending them in Dulbecco's phosphate buffered saline (PBS;pH 7) and centrifuging them down again. This procedure removed any sensitizer and polymer from the exterior of the cells and left only sensitizer on the inside of the cells. Its amount could be determined by visible spectroscopy as described above. The washed cells were finally resuspended in fresh growth medium containing no sensitizer and no polymer (25 mL). In the same way, the contents of flask B were divided into two equal portions ($B_1$, $B_2$). Part $B_1$ was reserved and part $B_2$ was washed with PBS as described for part $A_2$ and then resuspended in fresh growth medium containing neither polymer nor sensitizer. Flask C was divided into two equal portions $C_1$, $C_2$. The viability of the cells in flask $A_1$, $A_2$, $B_1$, $B_2$, $C_1$ and $C_2$ was checked.

For irradiation experiments, the contents of the flasks $A_1$, $A_2$, $B_2$ and $C_2$ were irradiated with white light for one hour. All cell preparations, including the controls ($B_1$, $C_1$) were incubated for a further 24 hours.

After a typical irradiation experiment, the cell viability was checked by counting the density of cells immediately after the 1 hour of irradiation and again 24 hours after irradiation has been stopped. Typical results are shown in the Table.

Table showing cell viability after irradiation and incubation for 24 hours.

|  | $A_1$ | $A_2$ | $B_2$ | $C_2$ |
|---|---|---|---|---|
| Percentage of dead cells before irradiation[a] | 4 | 4 | 3 | 5 |
| Percentage of dead cells immediately after irradiation[b] | 51 | 47 | 5 | 8 |
| Percentage of dead cells 24 hours after irradiation | 100 | 100 | 4 | 6 |

[a] These were the percentages of dead cells after 24 hours of incubation in the absence of light.

[b] These were the percentages of dead cells immediately after irradiation for 1 hour with white light.

[c] These were the percentages of dead cells after a further 24 hours on incubation following the 1 hour irradiation. The observation of 5–10 dead cells per 100 is quite normal for typical cell preparations in which no extraneous factors are at work. The controls $B_1$ and $C_1$ showed proportions of dead cells of only 5–8%.

Example of Delivery of a Cytotoxic Agent to Cultures of Cancer Cells

To Test the effects of cell cytotoxins.

TAXOL (paclitaxel) is a powerful cytotoxic agent but is very difficult to use because it is almost insoluble in water or blood plasma. For in vivo or in vitro use, it is generally dissolved in dimethyl sulphoxide (DMSO) or in a complex commercial pharmaceutical preparation. For the experiments described here, TAXOL (paclitaxel) was incorporated into an aqueous amphiphilic polymer solution exactly as described for the photosensitizer in part (i), except that the TAXOL (paclitaxel) was included in place of the sensitizer. The TAXOL (paclitaxel) concentration was varied over the range of 1 to 8nM. These carrier solutions were labeled "polymer" series. Similarly, the same range of TAXOL (paclitaxel) solution concentrations was prepared in neat dimethyl sulphoxide as solvent; these carrier solutions were labeled "DMSO" series. Finally, a series of commercially available pharmaceutical preparations was used, which contained TAXOL (paclitaxel) in the concentration range of 1 to 8 nM; these carrier solutions were labeled "commercial" series. Finally, a control series was used, in which only the amphiphilic polymer solutions were used but without containing any TAXOL (paclitaxel). The four series of solutions were compared for their cytotoxic action by a clonogenic cell survival assay using three human in vitro cell lines, viz., HELA (originally explanted from cancer of the cervix), HRT-18 (originally explanted from a lung cancer) and MGHU-1 (originally explanted from a bladder cancer). The results are shown graphically in FIGS. 1 to 3.

Figure 1:
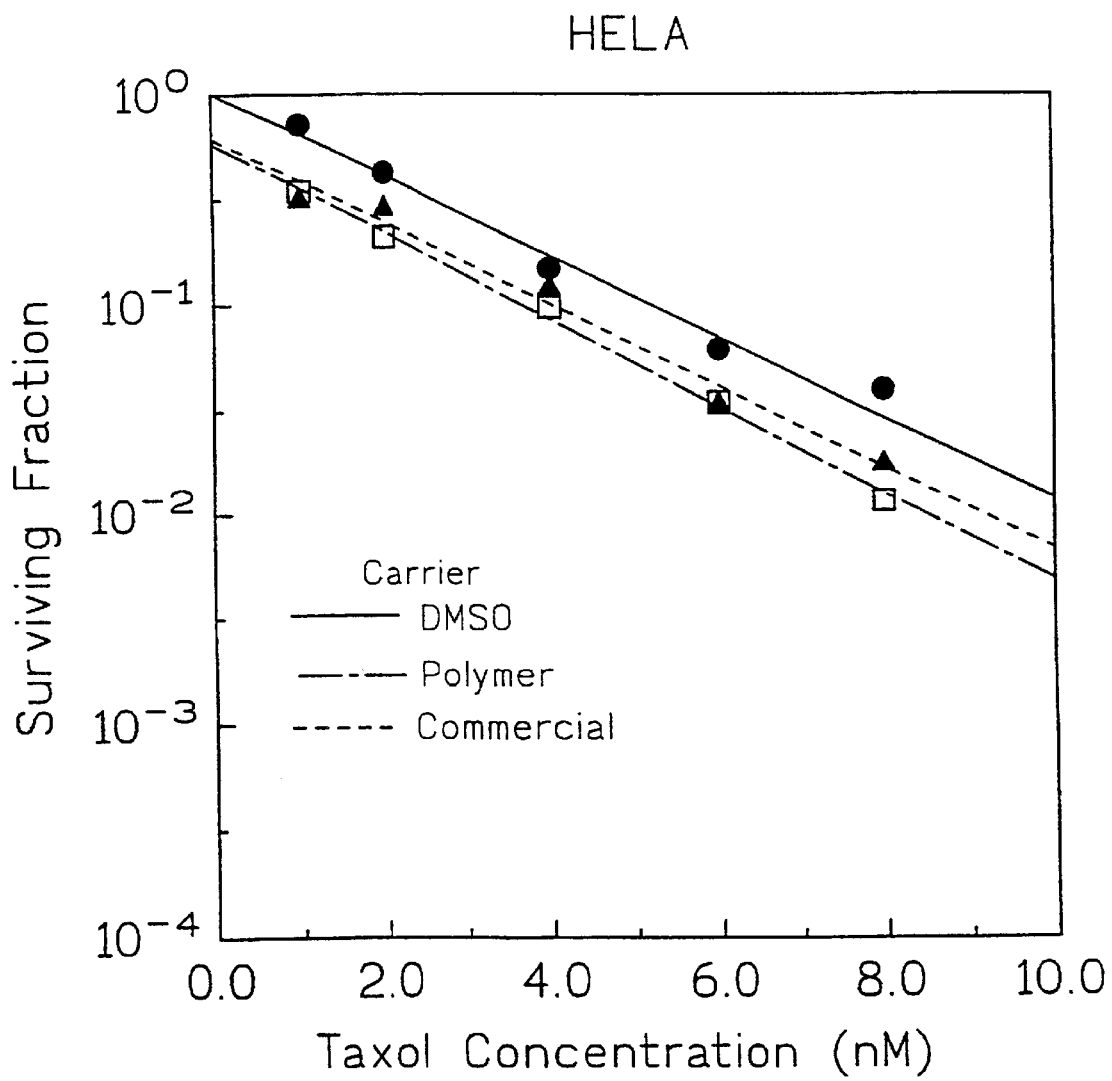
FIG. 1 illustrates the effect of the polymer in the delivery of TAXOL (paclitaxel) in a Hela cell line.
Figure 2:
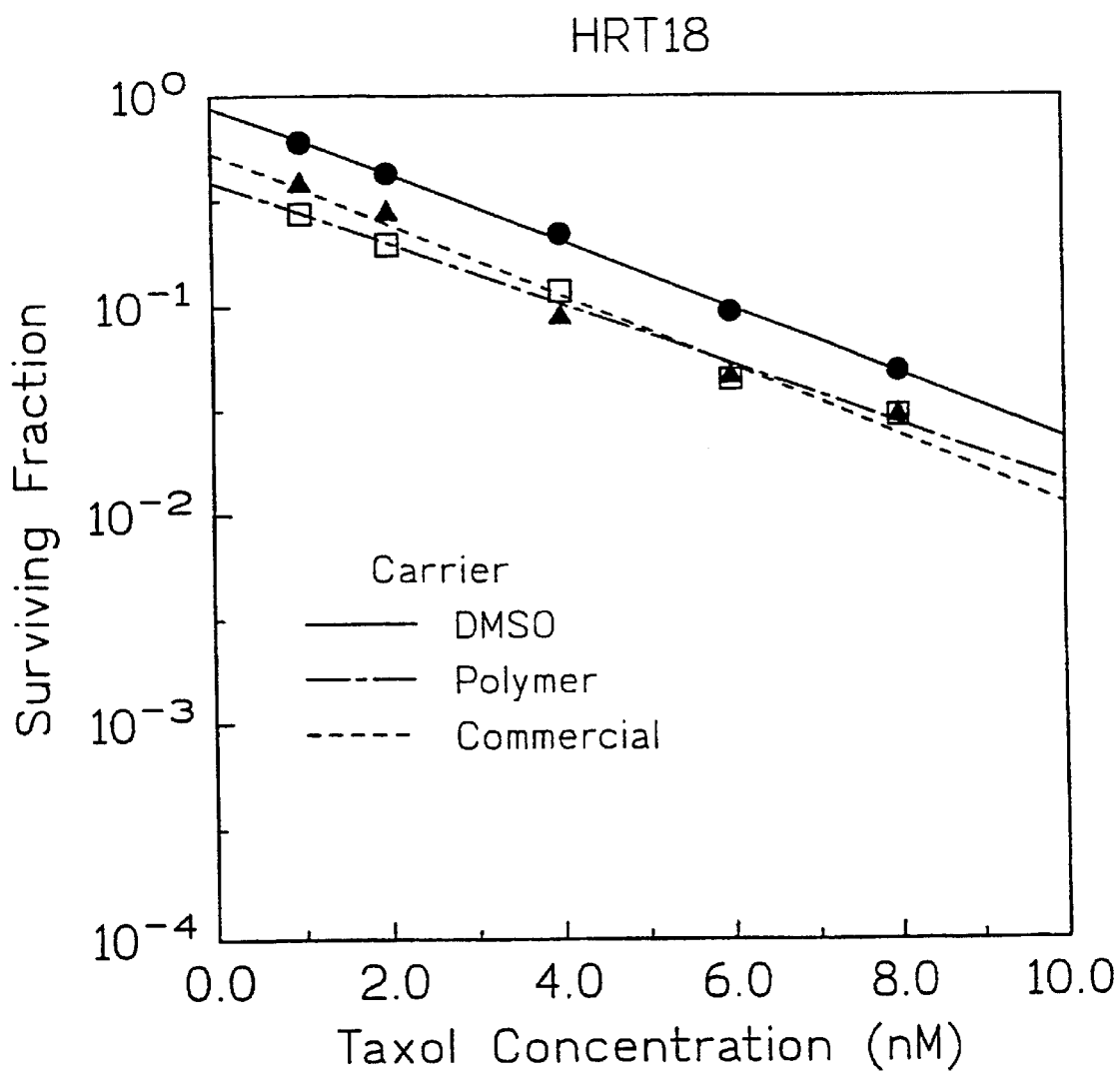
FIG. 2 illustrates the effect of the polymer in the delivery of TAXOL (paclitaxel) in a HRT-18 cell line.
Figure 3:
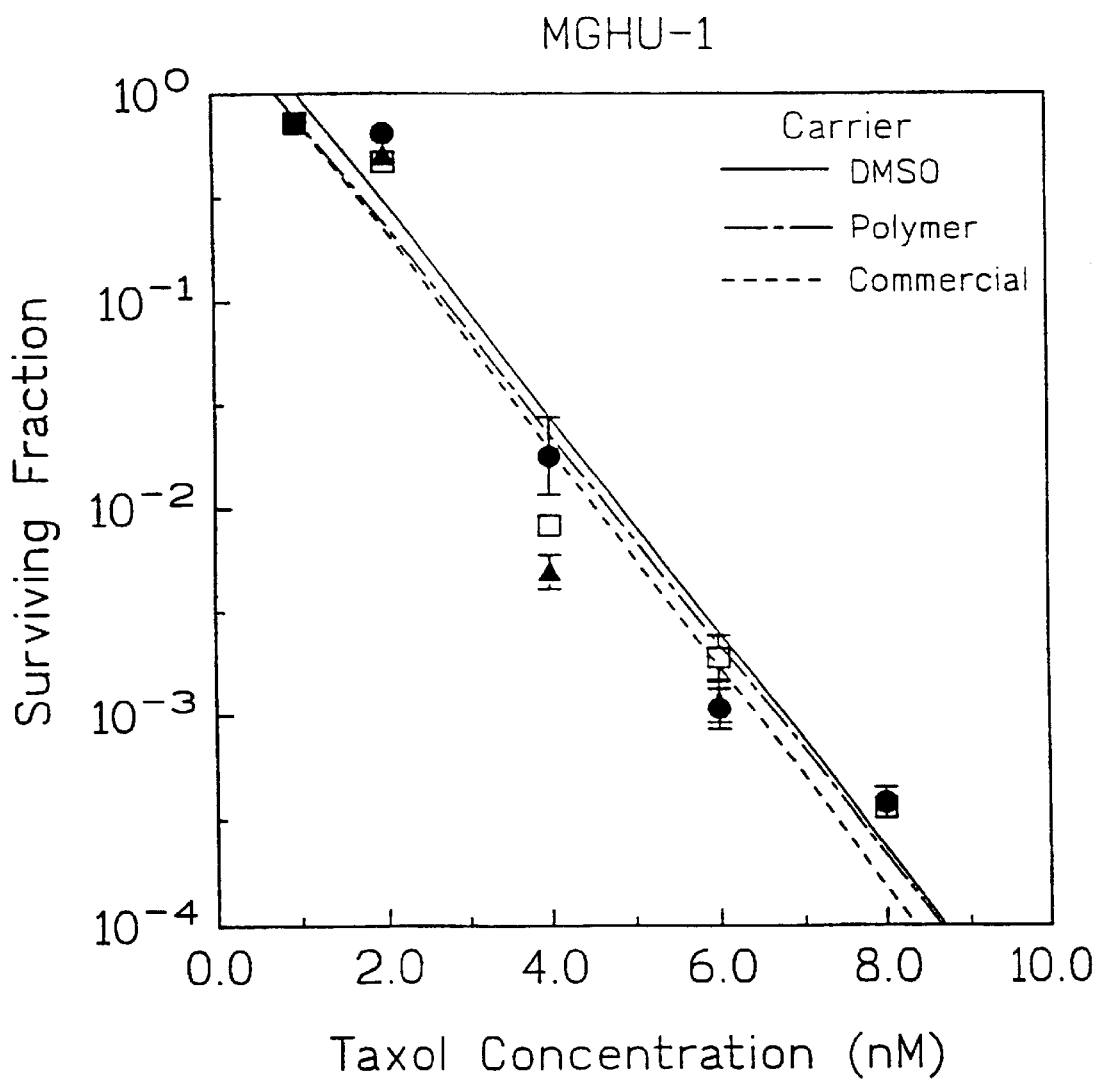
FIG. 3 illustrates the effect of the polymer in the delivery of TAXOL (paclitaxel) in a MGHU-1 cell line.

In the controls with no TAXOL (paclitaxel), the cells proliferated normally. At increasing concentrations of TAXOL (paclitaxel) in the commercial and DMSO series, the survival of the three cancer cell lines decreased steadily until at 8 mM the surviving fractions were about 0.1 to 0.01 in HELA and HRT-18, compared with an initial fraction equal to 1.0 but were only 0.0005 in MGHU-1. The "commercial" preparations were somewhat more effective than were the "DMSO" series. The "polymer" series behaved almost identically to the commercial series for all three cell lines, showing that these aqueous amphiphilic polymer solutions were equally as effective as the commercial or DMSO preparations. The controls showed that aqueous solutions of the amphiphilic polymer without TAXOL (paclitaxel) were inactive in cytosis and therefore that the observed effect with TAXOL (paclitaxel) was due entirely to the TAXOL (paclitaxel) and not the, carrier. The results of the assays are shown in the figures.

In a similar fashion, the water insoluble cytotoxic agent, amsacrine, eas shown to be effective for cytotoxicity of the above cell lines when it was incorporated into aqueous solutions of an amphiphilic polymer.

What is claimed is:

1. A composition of matter comprising a water-insoluble drug or other therapeutic or diagnostic agent that is carried internally within a hydraphobic or lipophilic pocket or pockets in a water-miscible amphiphilic polymer which comprises q monomer units of the formula $[((CHR)_n-(CRR^1)_m(CHR)_p)_v-A]$ and u monomer units of the formula $[((CHR)_r-(CRR^2)_s-(CHR)_t)_w-B],$ wherein A and B are independently CH2, or NH;
wherein n, m, p, r, s, t independently are any whole number as long as $(n+m+p)_v+(r+s+t)_w$ ranges from 1–1000, and the ratio v/w varies between 0.1 and 10.0;
wherein the values of q and u independently are from 1–10;
wherein each R, independently, is selected from the group consisting of H, alkyl, haloalkyl, hydroxyalkyl, alkenyl and alkynyl;
wherein $R^1$ is a hydrophobic moiety containing an aromatic hydrocarbon ring;
wherein $R^2$ is a hydrophobic moiety that provides water-solubility and is selected from the group consisting of —OH, a hydroxyalkyl, a polyoxyethylene moiety, a hydroxyphenyl, a substituted hydroxyphenyl, a pyrrolidine moiety, an N-oxide pyridine moiety, an N-oxide moiety, an N-oxide histidine moiety, a tryptophan moiety, a phenylalanine moiety, a tyrosine moiety, a phenyl sulphonate moiety, a naphthalene sulphonate moiety, an imidazole moiety, a water soluble naphthalene salt, an anthracene moiety, a phenanthrene moiety, a phenyl, a carbazole moiety, a xanthene moiety, an acridine moiety, a purine moiety, a pyridazine moiety, an indole moiety, —COOH, —COOM, $SO_3M$, —$NR_2$ and —$NR_3^+X^-$, wherein X is a halide ion and M is an alkali metal ion.

2. A composition of matter comprising a water-insoluble drug or other therapeutic or diagnostic agent as claimed in claim 1 wherein $R^1$ is selected from the group consisting of a toluene moiety, a methyl styrene moiety, a stilbene moiety, a pyridine moiety, a naphthalene moiety, an anthracene moiety, a phenanthrene moiety, a phenyl moiety, a histidine moiety, a tryptophan moiety, a phenylalanine moiety, a tyrosine moiety, an alkyl benzene moiety, a xylene moiety, a carbazole moiety, a xanthene moiety, an acridine moiety, a purine moiety, a pyridazine moiety and an indole moiety, and wherein R is independently selected from the group consisting of H, alkyl, and hydroxyalkyl.

3. A composition of matter comprising a water insoluble drug or other therapeutic or diagnostic agent as claimed in claim 2 wherein the amphiphilic polymer is selected from the group consisting of polystyrene sodium sulphonate-co-vinyl naphthalene; polyvinyl pyrrolidone-co-vinyl imidazole; and polynaphthalene sulphonate.

4. A composition of matter comprising a water insoluble drug or other therapeutic or diagnostic agent as claimed in claim 3 wherein the amphiphilic polymer is polystyrene sodium sulphonate-co-vinyl naphthalene.

5. A composition of matter as claimed in claim 2, wherein the amphiphilic polymer has a molecular weight of from 30,000 to 150,000 Daltons.

6. A composition of matter as claimed in claim 5 wherein the ratio of hydrophilic groups to hydrophobic groups is from 1:3 to 3:1.

7. A composition of matter as claimed in claim 1 wherein the water insoluble drug or other therapeutic or diagnostic agent is carried internally within a hydrophobic or lipophilic pocket or pockets defined by the conformation of said polymer in the aqueous environment.

8. A composition of matter as claimed in claim 7 wherein the water-insoluble drug or other therapeutic or diagnostic agent is packaged in an amount up from 5 to 20 molecules per macro molecule of amphiphilic polymer.

9. A composition of matter as claimed in claim 1 wherein the amphiphilic polymer is a random, graft or a block polymer.

10. A method of solubilising a water-insoluble drug or other therapeutic or diagnostic agent comprising carrying said drug or other therapeutic or diagnostic agent internally within a hydrophobic or lipophilic pocket or pockets in a water-miscible amphiphlic polymer which comprises q monomer units of the formula:

$[((CHR)_n-(CRR^1)_m-(CHR)_p)_v-A]$ and u monomer units of the formula $[((CHR)_r-(CRR^2)_s-(CHR)_t)_w-B],$ wherein A and B are independently CH2 or NH;
wherein n, m, p, r, s, t independently are any whole number as long as $(n+m+p)_v+(r+s+t)_w$ ranges from 1–1000, and the ratio v/w varies between 0.1 and 10.0;
wherein the values of q and u independently are from 1–10;
wherein each R independently is selected from the group consisting of H, alkyl, haloalkyl, hydroxyalkyl, alkenyl, and alkynyl;
wherein $R^1$ is a hydrophobic moiety containing an aromatic hydrocarbon ring;
wherein $R^2$ is a hydrophobic moiety that provides water-solubility and is selected from the group consisting of —OH, a hydroxyalkyl, a polyoxyethylene moiety, a hydroxyphenyl, a substituted hydroxyphenyl, a pyrrolidine moiety, an N-oxide pyridine moiety, an N-oxide moiety, an N-oxide histidine moiety, a tryptophan moiety, a phenylalanine moiety, a tyrosine moiety, a phenyl sulphonate moiety, a naphthalene sulphonate moiety, an imidazole moiety, a water soluble naphthalene salt, an anthracene moiety, a phenanthrene moiety, a phenyl, a carbazole moiety, a xanthene moiety, an acridine moiety, a purine moiety, a pyridazine moiety, an indole moiety, —COOH, —COOM, $SO_3M$, —$NR_2$ and —$NR_3^+X^-$, wherein X is a halide ion and M is an alkali metal ion.

11. A method of solubilising a water insoluble drug or other therapeutic or diagnostic agent as claimed in claim 10 wherein the amphiphilic polymer is polystyrene sodium sulphonate-co-vinyl naphthalene.

12. A method of treating cancer comprising administering to a human an effective amount of a water insoluble drug or other therapeutic or diagnostic agent in an amphiphilic polymer which comprises q monomer units of the formula $[((CHR)_n-(CRR^1)_m-(CHR)_p)_v-A]$ and u monomer units of the formula $[((CHR)_r-(CRR^2)_s-(CHR)_t)_w-B],$ wherein A and B are independently $CH_2$ or NH;
wherein n, m, p, r, s, t independently are any whole number as long as $(n+m+p)_v+(r+s+t)_w$ ranges from 1–1000, and the ratio v/w varies between 0.1 and 10.0;
where the values of q and u, independently are from 1–10;

wherein each R independently is selected from the group consisting of H, alkyl, haloalkyl, hydroxyalkyl, alkenyl, and alkynyl;

wherein $R^1$ is a hydrophobic moiety containing an aromatic hydrocarbon ring;

wherein $R^2$ is a hydrophilic moiety that provides water-solubility and is selected from the group consisting of —OH, a hydroxyalkyl; a polyoxyethylene moiety, a hydroxyphenyl, a substituted hydroxyphenyl, a pyrrolidine moiety, an N-oxide pyridine moiety, an N-oxide moiety, an N-oxide histidine moiety, a, tryptophan moiety, a phenylalanine moiety, a tyrosine moiety, a phenyl sulphonate moiety, a naphthalene sulphonate moiety, an imidazole moiety, a water soluble naphthalene salt, an anthracene moiety, a phenanthrene moiety, a phenyl, a carbazole moiety, a xanthene moiety, an acridine moiety, a purine moiety, a pyridazine moiety, an indole moiety, —COOH, —COOM, $SO_3M$, $—NR_2$ and $—NR_3^+X^-$, wherein X is a halide ion and M is an alkali metal ion.

13. A method of treatment according to claim 12 wherein the amphiphilic polymer is polystyrene sodium sulphonate-co-vinyl naphthalene.

14. A water solublised form of a water insoluble drug or other therapeutic or diagnostic agent which is carried internally within a hydrophobic or lipophilic pocket or pockets in a polymer of polystyrene sodium sulphonate-co-vinyl naphthalene.

15. A method of solubilising a water insoluble drug or other therapeutic or diagnostic agent comprising carrying said drug or other therapeutic or diagnostic agent internally within a hydrophobic or lipophilic pocket or pockets in a polymer of polystyrene sodium sulphonate-co-vinyl naphthalene.

16. A method of making a water soluble medicament, comprising mixing a water insoluble drug or other thereapeutic or diagnosticagent with a polymer of polystyrene sodium sulphonate-co-vinyl naphthalene in the manufacture of a medicament.

* * * * *